United States Patent
Agnus et al.

(10) Patent No.: US 6,656,929 B1
(45) Date of Patent: Dec. 2, 2003

(54) PHARMACEUTICAL COMPOSITION WITH A SYNTHETIC NATURAL PROGESTERONE AND OESTRADIOL BASE AND ITS PREPARATION PROCESS

(75) Inventors: Benoît Agnus, Bry sur Marne (FR); Antoine Besins, Paris (FR)

(73) Assignee: Laboratoires Besins Iscovesco, Paris (FR)

( * ) Notice: Subject to any disclaimer, the term of this patent is extended or adjusted under 35 U.S.C. 154(b) by 483 days.

(21) Appl. No.: 09/268,353

(22) Filed: Mar. 16, 1999

Related U.S. Application Data

(63) Continuation of application No. PCT/FR99/00515, filed on Mar. 8, 1999.

(30) Foreign Application Priority Data

Mar. 9, 1998 (FR) .......................................... 98 02830

(51) Int. Cl.$^7$ .............................................. A01N 45/00
(52) U.S. Cl. ..................................................... 514/170
(58) Field of Search .......................................... 514/170

(56) References Cited

U.S. PATENT DOCUMENTS

| 4,755,386 A | 7/1988 | Hsiao et al. ................. 424/435 |
| 5,633,242 A | 5/1997 | Oettel et al. .................. 514/17 |

FOREIGN PATENT DOCUMENTS

| EP | 0 371 466 | 6/1990 |
| FR | 2 399 243 | 3/1979 |
| WO | WO 95/05807 | 3/1995 |
| WO | 95/05807 | * 3/1995 |
| WO | WO 98/48782 | 11/1998 |

* cited by examiner

*Primary Examiner*—Barbara P. Badio
(74) *Attorney, Agent, or Firm*—Larson & Taylor PLC

(57) ABSTRACT

The object of this invention is a pharmaceutical composition with a synthetic natural progesterone and oestradiol base coming in the form of a tablet, characterised by the fact that it has a disintegration time of less than 15 minutes, preferably less than 10 minutes, and more preferably still less than 5 minutes.

13 Claims, 4 Drawing Sheets

PHARMACEUTICAL COMPOSITION WITH A SYNTHETIC NATURAL PROGESTERONE AND OESTRADIOL BASE AND ITS PREPARATION PROCESS

This application is a continuation of PCT/FR99/00515 filed Mar. 8, 1999.

FIELD OF THE INVENTION OF THE INVENTION

The object of the present invention is a pharmaceutical composition with a synthetic natural progesterone and oestradiol base coming in the form of a tablet, as well as a method for its preparation.

In the context of the present invention, "synthetic natural progesterone" is understood to mean a synthesized progesterone the chemical formula of which corresponds to the "natural" progesterone, such as is found in the female body. On the other hand, "synthetic progestagens" are entirely synthetic molecules such as trimegestone, norethisterone and others, the structure of which does not correspond to that of the natural progesterone.

Menopause in women can cause, indeed aggravate, certain pathologies such as oesteoporosis or cardiovascular illnesses.

Oestrogens, particularly oestradiol, are then prescribed in order to reduce these harmful consequences of menopause. But the administering of oestrogens can itself cause other undesirable effects.

It is therefore usual to combine it with a progesterone treatment in order to avoid risks of endometrical hyperplasia in particular.

It is obviously advantageous to be able to offer women these two active principles combined in the same drug in order to enable absorption in a single dose.

BACKGROUND OF THE INVENTION

Drugs with a progesterone and oestradiol base in the form of tablets are already on the market. However, all the tablets known to date use synthetic progestagens, which do not have all the therapeutic effects of synthetic natural progesterone and may even have undesirable effects. The use of synthetic natural progesterone enables the effects, in particular hepatotoxic effects, of synthetic progestagens to be avoided.

With regard to natural progesterone, the Applicant Company has already perfected a drug, which is very successful at the therapeutic level. This drug comes in the form of a capsule containing micronized synthetic natural progesterone in an oil suspension. This drug is sold under the brand name UTROGESTAN.

In view of the very good results which this drug gives when it is combined with a conventional oestradiol tablet in the treatment of inconveniences associated with menopause, it would be very attractive to have a tablet with a natural progesterone and oestradiol base having a bioequivalence relative to the UTROGESTAN capsules administered in combination with an oestradiol tablet.

However it so happens that developing such a tablet causes a certain number of problems.

These problems are essentially due to the fact that, in order to be effective, natural progesterone must be used in much stronger dosages than the synthetic progestagens, i.e. 50 or 60 times more of the active principle relative to the tablet containing synthetic progestagens. The consequence is that the ratio between natural progesterone and oestradiol is about 100/1, causing problems of homogeneity in the mixture of the active principles, in the tablets as well as during their manufacture.

Another consequence lies in the percentage of excipients that can be included in the tablets. Indeed, because of the significant quantity of natural progesterone, it is necessary to considerably decrease the excipient content in view of the constraints in size and weight appropriate to tablets intended to be administered orally and/or vaginally.

It is known that excipients in the tablets play various roles. They serve to increase the stability of the active principles, to obtain a particular release profile according to their nature, but they are used above all to facilitate the compression of the different ingredients in order to obtain a tablet having good characteristics of hardness, disintegration and dissolution.

OBJECTS AND DESCRIPTION OF THE INVENTION

Following much work and research, the Applicant Company has succeeded in developing a new tablet with a natural progesterone and oestradiol base, meeting the homogeneity requirements of the mixture and containing only small quantities of excipients, thus making it possible to obtain tablets of a size and weight entirely acceptable for oral and/or vaginal administration.

Moreover, the Applicant Company has found that when these tablets have a particular disintegration profile, they also have a bioequivalence to the UTROGESTAN capsules combined with an oestradiol tablet, which has been demonstrated by a pharmacokinetic study comparing the two treatments. This profile is characterised by a disintegration time of less than 15 minutes, preferably less than 10 minutes, and more preferably still less than 5 minutes.

The disintegration time of the tablets is measured in a "D" test. According to this "D" test, a tablet according to the invention is placed in a one litre beaker containing 700 ml of distilled water brought to a temperature of 37° C., and subjected to an alternating vertical motion. The time necessary for a total loss of cohesion is measured.

The invention therefore concerns a pharmaceutical composition with a natural progesterone and oestradiol base in tablet form, characterised by the fact that it has a disintegration time of less than 15 minutes, preferably less than 10 minutes, and more preferably still less than 5 minutes.

The weight ratio between the oestradiol and the progesterone is between 5/100 and 1/100, this ratio being expressed as a function of the total weight of the progesterone in the tablet.

The homogeneity of the mixture and the oestradiol/progesterone ratio were obtained by means of a wet granulation process. The oestradiol is incorporated in a binding solution before being subjected to a wetting-granulation stage, thus guaranteeing a good homogeneity of the mixture as well as a good dosage of this steroid.

Although the tablets developed by the Applicant Company contain significantly lower quantities of excipients than tablets of the prior art, they nevertheless have excellent characteristics of stability, hardness, disintegration and dissolution.

According to a preferential method of producing the invention, the pharmaceutical composition in tablet form according to the invention is characterised by the fact that the content of excipients is at most 20%, preferably at most 17%, and more preferably still at most 15%, the percentages being expressed by weight relative to the total dry matter of the tablet.

As examples of excipients that can be used in the pharmaceutical composition according to the invention, diluents, disintegrating agents, lubricants, binding agents and stripping agents may be mentioned.

Examples of diluents are starches, polyols and celluloses. Preferably, the tablet according to the invention contains in particular sodium carboxymethylcellulose.

As examples of disintegrating agents, carboxymethylcelluloses, alginic acid as well as its sodium salt, and starches may be mentioned. Preferably, the tablet according to the invention contains reticulated sodium carboxymethylcellulose not only as thinner but also thanks to its disintegrating agent qualities, as well as for its strong absorbent power.

The preferred lubricant in the context of this invention is magnesium stearate.

Of the preferred binding agents in the context of this invention, one may mention polyvinylpyrollidones, but also sodium carboxymethylcellulose. This product not only enables a stable oestradiol suspension to be obtained, but also a quasi-immediate release of the active principle. Moreover it is very easy to use.

The preferred stripping agents in the context of this invention are methylhydroxypropylcellulose and polyethyleneglycol 600. It is in fact necessary to carry out the stripping in order to avoid a pure contamination.

An advantage of the tablet according to this invention is that it has a dissolution profile such that the released progesterone content is at least 75% and that the released oestradiol content is at least 75% in 15 minutes, preferably in 10 minutes, and more preferably still in 5 minutes.

The tablet according to the invention has a hardness between 10 and 80 N, preferably between 20 and 70 N, and more preferentially still between 30 and 60 N.

The invention also concerns a process for the preparation of a pharmaceutical composition with a progesterone and oestradiol base in the form of a tablet. This process is characterised by the fact that:

- a wetting suspension is prepared which is mixed with an oestradiol suspension,
- a first mixture of progesterone and diluent is prepared,
- a second mixture of the first mixture and the wetted oestradiol suspension is prepared,
- a second wetting of the product of this second mixture is carried out,
- a granulation of the product of the wetting is carried out, in order to obtain a granular product,
- disintegrating agents and diluents are added to the granular product in order to obtain a third mixture,
- a lubricant is added to the third mixture in order to obtain a fourth mixture,
- a compression of the fourth mixture is carried out in order to obtain tablets,
- stripping of the tablets is carried out.

According to a preferential method of producing the invention, the granulation is followed by unclotting, drying, then grading.

Figure 1:
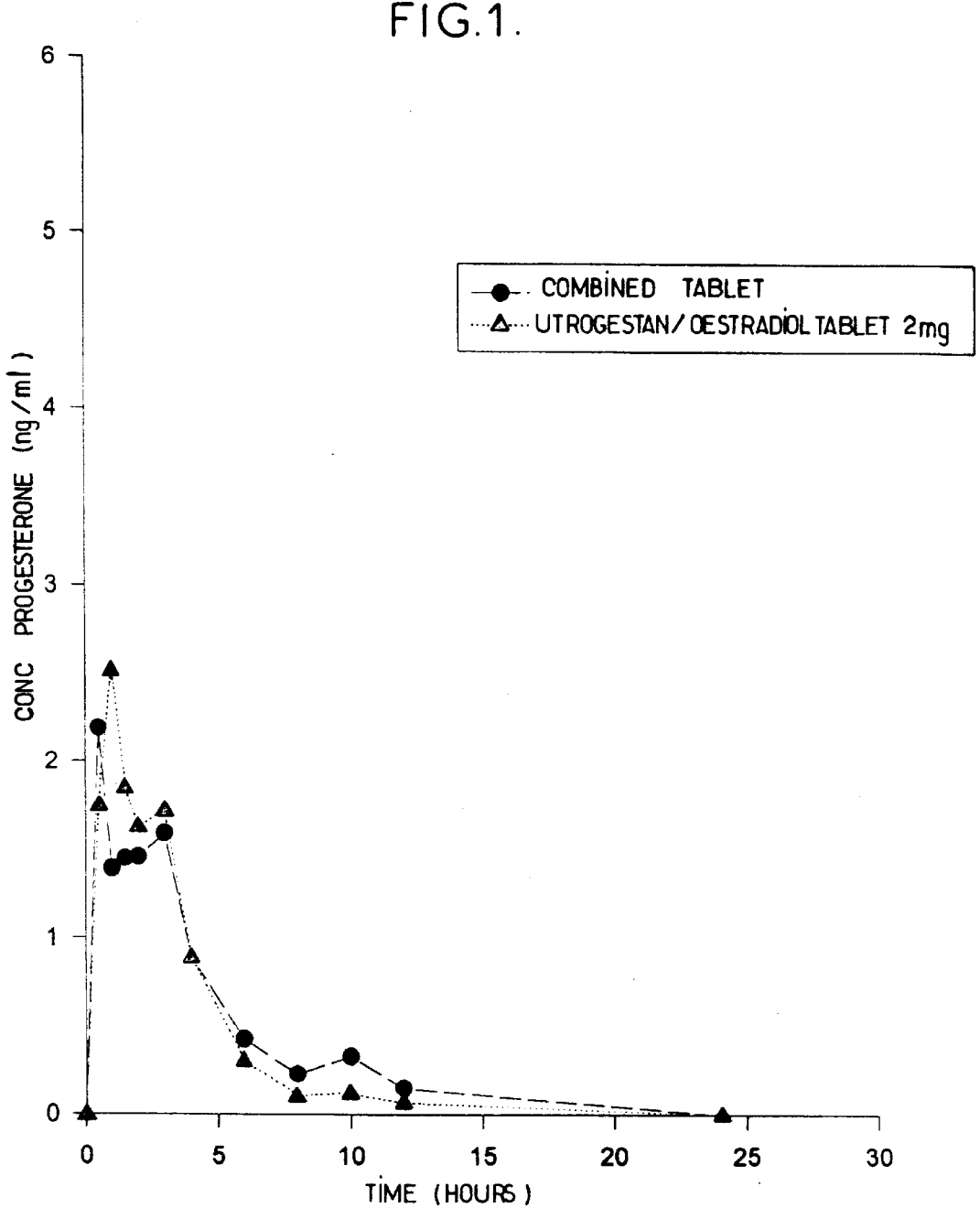
FIGS. 1 and 2 show the results of a pharmacokinetic study carried out on six menopaused Caucasian women less than 70 years old, which compares the tablets of the present invention with UTROGESTAN capsules administered in combination with an oestradiol tablet.
Figure 2:
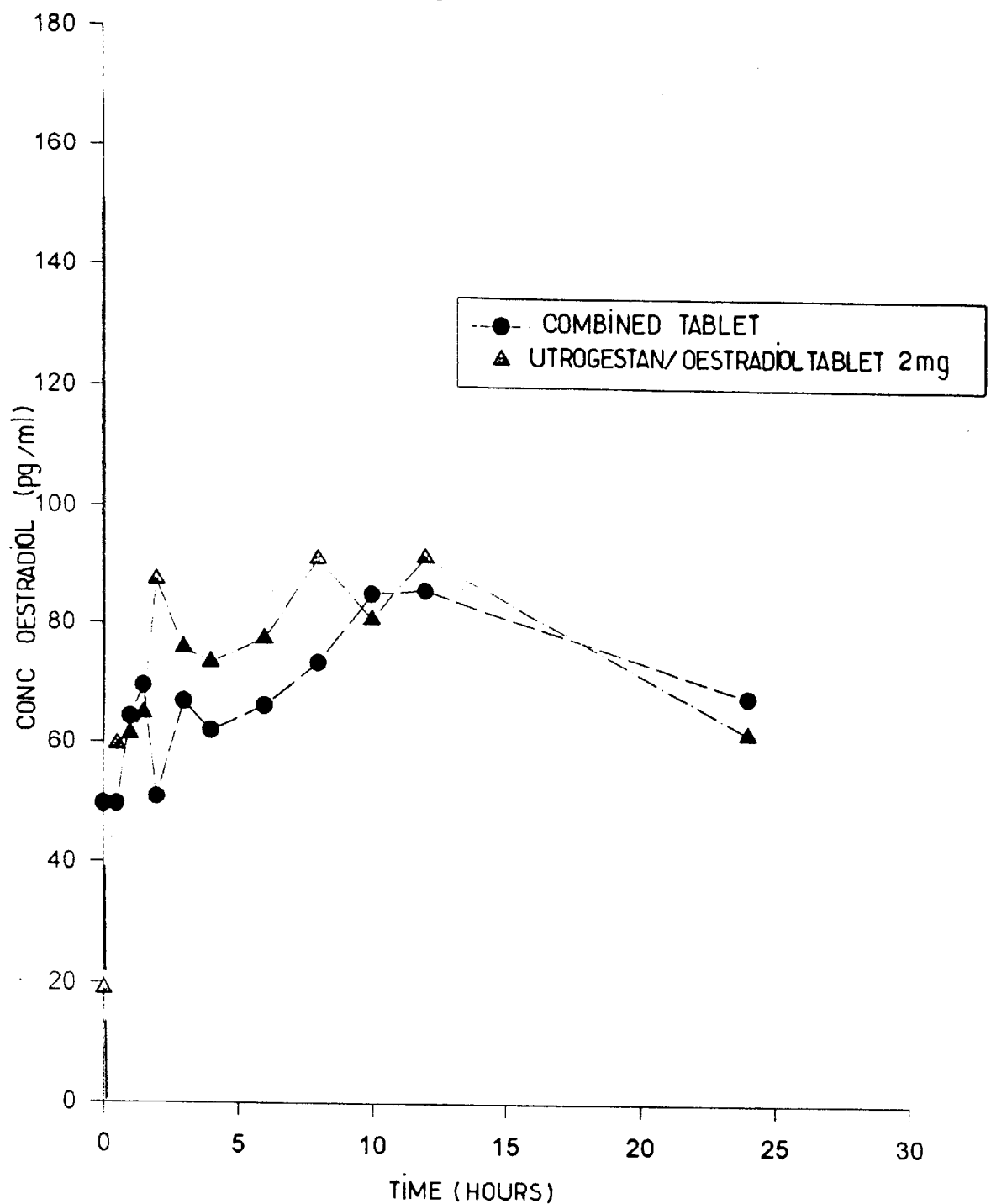

These Figures confirm the good correlation between a tablet combining progesterone and oestradiol, versus an UTROGESTAN capsule and an oestradiol tablet.

MORE DETAILED DESCRIPTION

The invention will be better understood with the help of the non-restrictive examples described below.

EXAMPLE 1 PHARMACEUTICAL COMPOSITION ACCORDING TO THE INVENTION

The compositions of tablets with a natural progesterone and oestradiol base according to the invention containing 101 mg of active principles are given in Table I below.

TABLE 1

| NAME OF CONSTITUENT | FUNCTION | QUANTITY mg/tablet |
|---|---|---|
| Micronized progesterone | Progestagen | 100 |
| Micronized oestradiol | Oestrogen | 1 |
| Sodium carboxymethyl cellulose | Binder | 3.20 |
| Reticulated sodium carboxymethyl cellulose | Disintegrating diluent | 10.75 |
| Magnesium stearate | Lubricant | 1.16 |
| Methylhydroxypropyl cellulose | Stripping agent | 1.80 |
| Polyethylene glycol 600 | Stripping agent | 0.20 |

EXAMPLE 2

PREPARATION OF TABLETS ACCORDING TO THE INVENTION

A batch of tablets containing 100 mg of natural progesterone and 1 mg of oestradiol per tablet were prepared as described below.

a) Preparation of the Progesterone Mixture 10 kg of micronized progesterone (obtained from the DIOSYNTH Company, at Oss, Netherlands) and 500 g of reticulated sodium carboxymethylcellulose are mixed in the vat of a BONNET type planetary granulator mixer equipped with a Lyre type agitation spindle, for 10 minutes, in order to obtain a homogeneous mixture.

b) Preparation of the Oestradiol Wetting Suspension 6 litres of purified water are put into a stainless steel container. This is agitated by means of a TURBOTEST RAYNERI mixer equipped with a deflocculation type agitating spindle.

320 g of sodium carboxymethyl cellulose (marketed under the brand name BLANOSE 7LF by the HERCULES Company) are gradually poured into the container, and then it is homogenized until the BLANOSE has completely dissolved. To this BLANOSE solution are added 102 g of oestradiol. This is added for 45 minutes until the oestradiol is completely dispersed.

c) Wetting

The oestradiol wetting solution is trickled onto the powder mixture contained in the BONNET mixer, the LYRE type spindle being programmed on speed 1 for 5 minutes.

d) Granulation

The mixture is homogenized for 30 minutes after the end of the wetting in order to obtain a granular powder.

e) Drying

Drying is carried out in an oven at 40° C. for 6 hours.

f) Grading

Grading of the granular powder is carried out by means of a FREWITT oscillating granulator equipped with a stainless steel sieve with a mesh diameter of 1250 μm.

g) Addition of the Disintegrating Agents and Diluents to the Granular Product

To 10 kg of the granular product are added 550 g of reticulated sodium carboxymethyl cellulose in the vat of a ROUE RÖHN mixer and this is mixed for twice five minutes.

To the mixture thus obtained are added 112 g of magnesium stearate and this is mixed for three minutes in order to obtain the final mixture.

h) Compression of the Final Mixture

Compression of the final mixture is carried out on a FROGERAIS MR 200 type rotary compressing machine, equipped with stamps. Adjustment of the machine is made so as to obtain tablets with a unit mass of 116 mg and a disintegration time less than about 5 minutes and a hardness of about 40 N.

i) Stripping

The stripping solution is prepared by adding 270 g of methylhydroxypropylcellulose (marketed under the name of PHARMACOAT 606 by the SEPPIC Company) and 30 g of polyethylene glycol 600 with 3.2 litres of purified water. It is mixed for 1 hour, then the tablets are sprayed with a STELLERLUPT type Airless gun and a 0.5 mm diameter nozzle.

The tablets obtained are packaged in thermally moulded blister strips, consisting of a PVC sheet with a thickness of 250 μm, sealed with an aluminium sheet with a thickness of 20 μm.

A stability study has been carried out on the tablets thus prepared.

No change in the galenic and analytical parameters was observed at the end of this period, thus demonstrating the good stability of the tablets according to the invention.

EXAMPLE 3

DISINTEGRATION TIME OF THE TABLETS ACCORDING TO THE INVENTION

A tablet manufactured according to the method described in example 2 was placed in a beaker containing 700 ml of distilled water brought to a temperature of 37° C. The disintegration time corresponding to a total loss of cohesion was 4 minutes.

EXAMPLE 4

DISSOLVING TIME OF THE TABLETS ACCORDING TO THE INVENTION 6 dissolving vats of 1000 ml capacity were used.

For the Progesterone

In each of the vats, a tablet was placed in a dissolving medium containing 1000 ml of an aqueous solution containing 1% (m/v) of sodium laurylsulfate. Then the solution was agitated in each vat by means of a PHARMATEST type PTWS III dissolving apparatus with rotating paddles. The paddles were immersed in the dissolving medium with a distance of 25 mm ±2 mm between the paddle and the vat bottom. The paddles were agitated at 75 revs per minute.

1 ml of dissolving medium was sampled every 5 minutes in each of the vats.

Each sample was measured by HPLC (=280 ηm) after injection of 20 μl of solution to be analysed.

Figure 3:
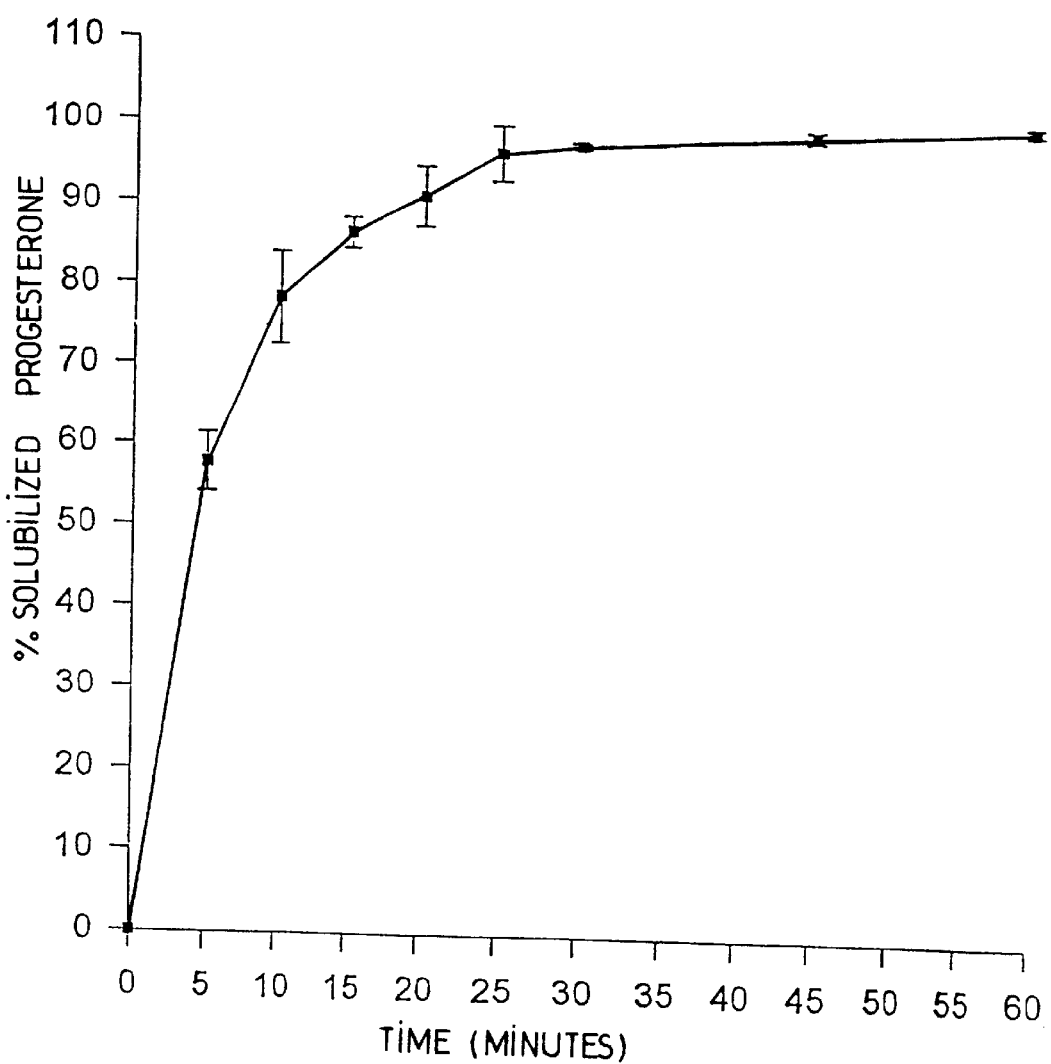
FIG. 3 shows the dissolution profile obtained for progesterone.

The curve given in FIG. 3 shows the dissolution profile obtained. At least 75% of the progesterone is released in 15 minutes of dissolution.

For the Oestradiol

In each of the vats, 2 tablets were placed in a dissolving medium containing 500 ml of an aqueous solution containing 0.5% (m/v) of sodium laurylsulfate. The solution was agitated in each vat by means of a PHARMATEST type PTWS III dissolving apparatus with rotating paddles. The paddles were immersed in the dissolving medium with a distance of 25 mm ±2 mm between the paddle and the bottom of the vat. The paddles were agitated at 75 revs per minute.

1 ml of the dissolving medium was sampled every 5 minutes in each of the vats.

Each sample was measured out by HPLC (=280 ηm) after injection of 20 μl of solution to be analysed.

Figure 4:
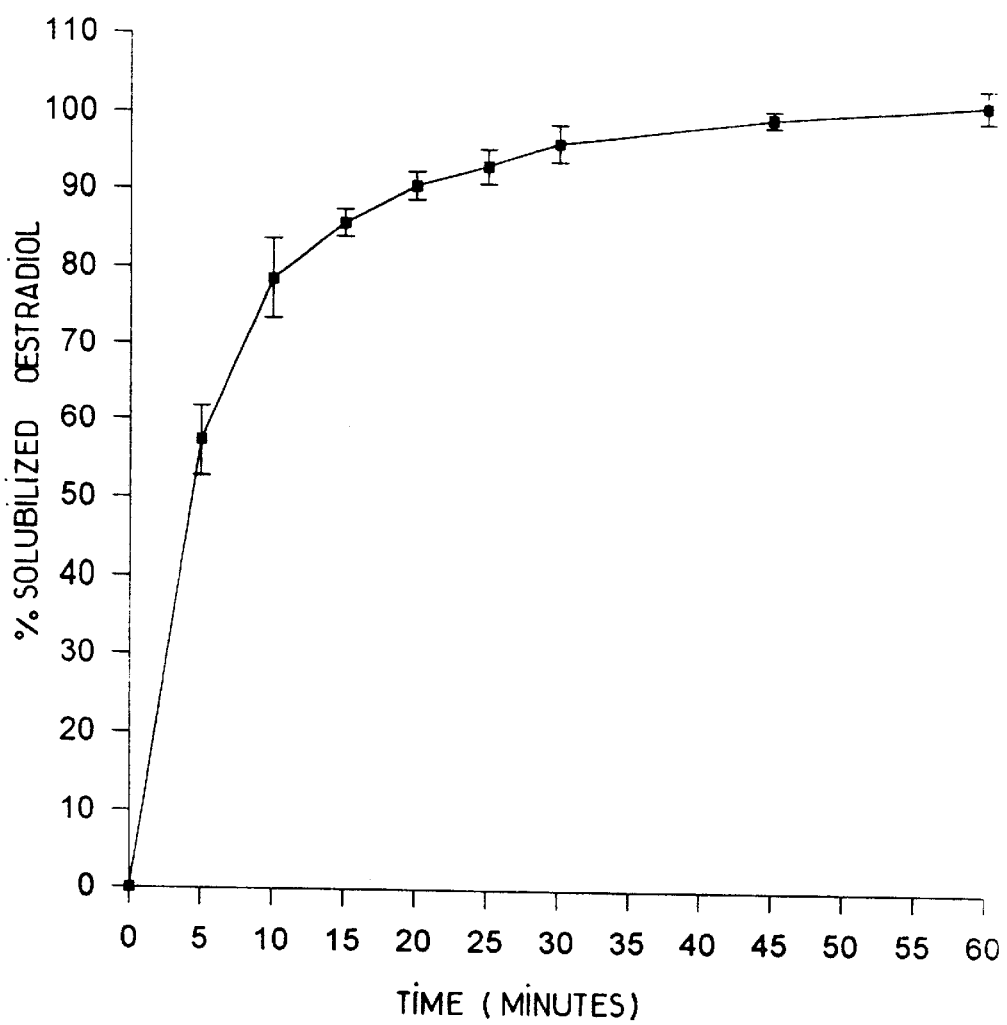
FIG. 4 shows the dissolution profile obtained for oestradiol.

The curve given in FIG. 4 shows the dissolving profile obtained. At least 75% of the oestradiol is released in 15 minutes of dissolving.

What is claimed is:

1. A pharmaceutical composition in the form of a tablet comprising synthetic natural progesterone, and oestradiol, said tablet having an excipient content of no more than 20% by weight based on total dry matter weight of the tablet, said tablet having a disintegration time of less than 15 minutes.

2. The pharmaceutical composition according to claim 1, having a disintegration time of less than 10 minutes.

3. The pharmaceutical composition according to claim 2, having a disintegration time of less than 5 minutes.

4. The pharmaceutical composition according to claim 1, wherein the weight ratio between the oestradiol and the synthetic natural progesterone is between 5/100 and 1/100, the ratio being expressed as a function of the total weight of the progesterone in the tablet.

5. The pharmaceutical composition according to claim 1, wherein the tablet has an excipient content of no more than 17%.

6. The pharmaceutical composition according to claim 5, wherein the tablet has an excipient content of no more than 15%.

7. The pharmaceutical composition according to claim 1, having a dissolution profile such that released progesterone content is at least 75% and released oestradiol content is at least 75% in 15 minutes.

8. The pharmaceutical composition according to claim 7, having a dissolution profile such that the released progesterone content is at least 75% and the released oestradiol content is at least 75% in 10 minutes.

9. The pharmaceutical composition according to claim 8, having a dissolution profile such that the released progesterone content is at least 75% and the released oestradiol content is at least 75% in 5 minutes.

10. The pharmaceutical composition according to claim 1, having a hardness between 10 and 80 N.

11. The pharmaceutical composition according to claim 10, having a hardness between 20 and 70 N.

12. The pharmaceutical composition according to claim 11, having a hardness between 30 and 60 N.

13. The pharmaceutical composition according to claim 1, containing diluents, disintegrating agents, lubricants, binding agents and stripping agents.

* * * * *